United States Patent [19]
MacMillan et al.

[11] Patent Number: 5,062,850
[45] Date of Patent: Nov. 5, 1991

[54] AXIALLY-FIXED VERTEBRAL BODY PROSTHESIS AND METHOD OF FIXATION

[75] Inventors: Michael MacMillan, Gainesville, Fla.; Regis Haid, Jr., San Antonio, Tex.

[73] Assignee: University of Florida, Gainesville, Fla.

[21] Appl. No.: 465,419

[22] Filed: Jan. 16, 1990

[51] Int. Cl.$^5$ .............................................. A61F 2/44
[52] U.S. Cl. ........................................ 623/17; 606/61
[58] Field of Search ............................ 623/17; 606/61

[56] References Cited

U.S. PATENT DOCUMENTS

| | | | |
|---|---|---|---|
| 4,309,777 | 1/1982 | Patil | 623/17 |
| 4,599,086 | 7/1986 | Doty | 623/17 |
| 4,636,217 | 1/1987 | Ogilvie et al. | 606/61 |
| 4,657,550 | 4/1987 | Daher | 623/17 |
| 4,759,769 | 7/1988 | Hedman et al. | 623/17 |
| 4,874,389 | 10/1989 | Downey | 623/17 |
| 4,932,975 | 6/1990 | Main et al. | 623/17 |

FOREIGN PATENT DOCUMENTS 3023353  4/1981  Fed. Rep. of Germany ........ 623/17

Primary Examiner—David J. Isabella
Assistant Examiner—Debra S. Brittingham
Attorney, Agent, or Firm—Spensley Horn Jubas & Lubitz

[57] ABSTRACT

A vertebral body prosthetic device for replacing a surgically removed natural vertebral body and a method for its fixation to thereby reconstruct a patient's spinal column. The inventive device generally comprises upper and lower endplates separated by a plurality of support columns or posts. The device is dimensioned to fit completely within the patient's vertebral column and is fixed using axially-oriented screws.

15 Claims, 2 Drawing Sheets

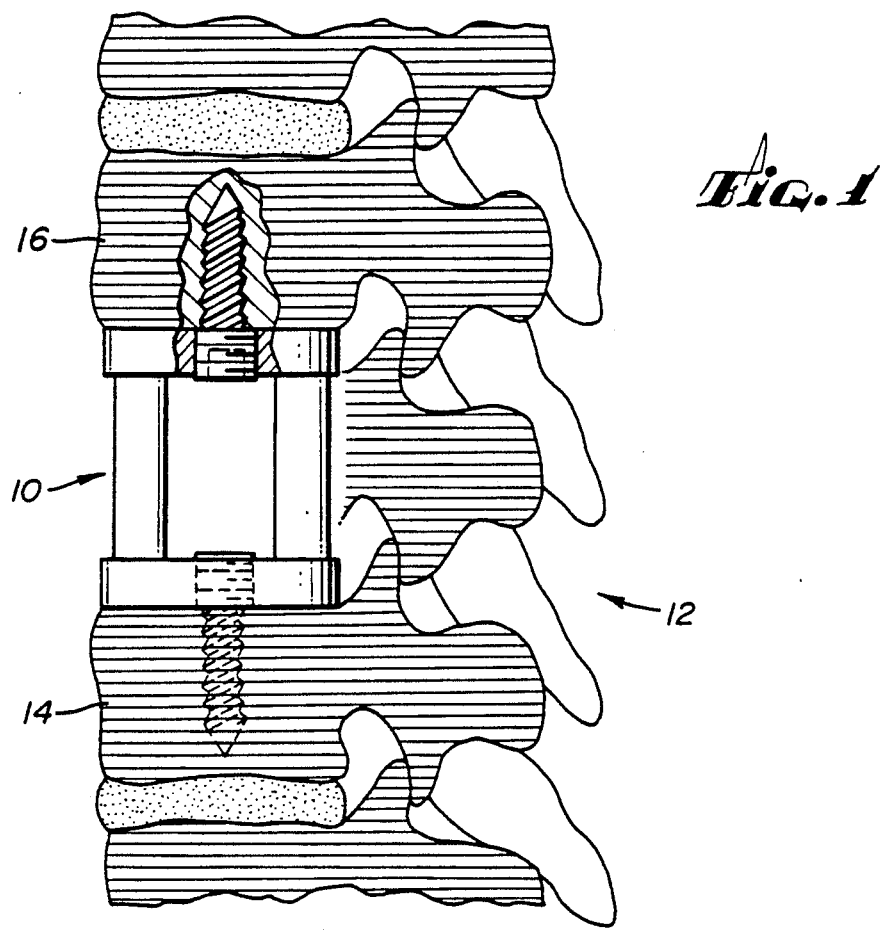
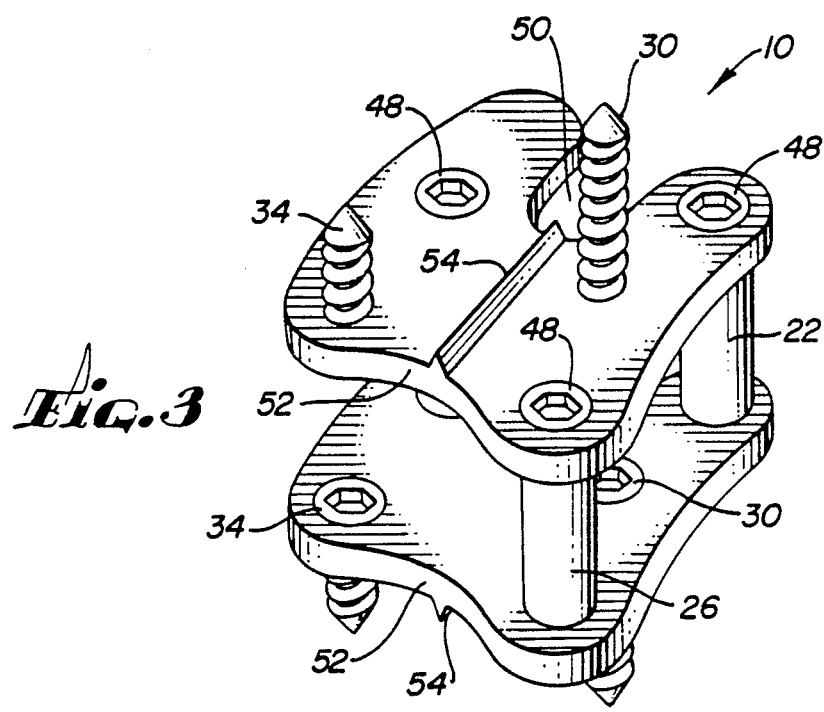

AXIALLY-FIXED VERTEBRAL BODY PROSTHESIS AND METHOD OF FIXATION

BACKGROUND OF THE INVENTION

1. Field of the Invention

This invention relates generally to prosthetic implant devices for the spinal column, and more particularly to prosthetic devices for replacing unstable and/or surgically excised vertebral bodies of the thoracolumbar region of the spine, and methods for their insertion and fixation.

2. Related Art

The treatment of acute and chronic spinal cord injuries is rapidly advancing. Many new techniques designed to return function to an injured spinal cord are currently undergoing clinical studies. These new techniques generally require that the spinal cord be adequately decompressed. Typically, portions of the anterior vertebral column (i.e., the vertebral body) are removed to access the anterior portion of the spinal cord.

Anterior surgery is the preferred method for correcting vertebral body injuries for several reasons. First, the material causing the injury usually lies anteriorly and is therefore most easily removed from this aspect. Also, the motor tracks lie predominantly on the anterior aspect of the spinal cord and may more easily be restored from this approach. Finally, it is generally agreed that decompression of the neural tissue to facilitate a patient's recovery from acute traumatic spinal cord injuries is best accomplished through an anterior approach to the spine.

Unfortunately, the amount of anterior vertebral bone necessarily removed to expose the relevant section of the spinal cord or to achieve adequate decompression greatly increases the instability of the anterior and middle spinal columns. It is essential to the success of most spinal cord injury treatment techniques that the bony vertebral column be reconstructed to prevent instability or compression from compromising the neural repair.

Currently, the spinal column is typically reconstructed by grafting bone into the defect created by removal of anterior vertebral bone. Stabilizing instrumentation was then applied posteriorly through a second surgical procedure. The disadvantage of this method is the need for the second procedure from a different approach. Also, immediate post-operative stabilization of the spinal column is not possible using this technique since fusion of the grafted bone with the adjacent vertebrae requires three to six months. Patients undergoing spinal surgery were therefore typically required to restrict their movement and wear external spine stabilization devices post-operatively until the graft had adequately healed.

Alternatively, a number of surgical implants have been used to anteriorly stabilize the spinal column. Most of these stabilizing devices include a bridge member which spans the vertebral defect (i.e., the site of an injured vertebrae or the void where a vertebral body has been removed). The devices typically include lateral supports by which they are secured to the lateral surfaces of the neighboring vertebrae using bone screws.

Lateral attachment of the devices, however, places the bone screws in a perpendicular orientation to the major axis of flexion and extension of the spinal column. It has been discovered that in this orientation, the bone screws are prone to dislodgement during application of bending and torsional forces. Additionally, since the mechanical forces applied to the devices when the spine is moved are greatest at the lateral attachment points, the bone screws may fracture the vertebral bodies to which they are attached. Also, the supports with which the devices are secured in place extend beyond the confines of the spinal column. Impingement against adjacent visceral and vascular structures may therefore occur, potentially causing serious complications. Finally, the laterally applied devices still require the placement of a structural bone graft in the spinal column.

Other available prosthetic devices comprise turnbuckle-like articulating members secured to adjacent vertebral bodies with axial pins. These devices are installed by positioning them into the void left after a vertebral body has been removed and then turning the turnbuckle to drive the pins into the subjacent and suprajacent vertebrae. While these devices are fully embedded within the spinal column upon installation, a major disadvantage of these devices again lies in their instability. Specifically, these devices are prone to tilting upon application of the mechanical forces generated by spinal movements, resulting in eventual dislodgement. Furthermore, the articulating components of these devices are known to fail through fatigue and wear. For these reasons, these devices do not present a permanent stabilizing solution.

A need remains for an anterior vertebral body prosthetic device which provides immediate post-operative stabilization of the spinal column and which is also suitable for permanent implantation.

SUMMARY OF THE INVENTION

The present invention provides a vertebral body prosthesis and a method for its installation and fixation to thereby reconstruct a patient's spinal column after a vertebral body in the thoracolumbar region of the spine has been surgically removed. The device provides immediate post-operative stabilization of the spinal column and is designed for permanent implantation.

The inventive device generally comprises upper and lower endplates separated by a plurality of support columns or posts. Each of the endplates is dimensioned to fit completely within the patient's vertebral column in the dorsi-lumbar region of the spine and includes at least two threaded holes for receiving an axially-oriented fixation screw and an axially-oriented anti-rotation screw, respectively. Additionally each endplate is preferably provided with two lateral passages, one connecting to each of the threaded holes, respectively. These lateral passages are dimensioned to receive small set screws which help fix the axially-oriented screws in place.

In a preferred embodiment of the invention, the endplates have a notched design. Specifically, each endplate is provided with one or more recessed areas. One of the recessed areas forms a deep notch which may be used to embrace a temporary strut or instrument which, in turn, may be used to maintain the correct anatomical distance between the subjacent and suprajacent vertebrae before and during installation of the inventive prosthetic device. This notch may subsequently serve as a bone grafting site to bridge bone across that side of the vertebral body defect.

The second cut-out area forms a more shallow notch on the contralateral side of the prosthetic device. This second notch is provided as a site for bone placement to bridge across this side of the vertebral body defect.

In the preferred embodiment of the invention, a number of differently sized endplates and support columns are provided. The device is assembled for each individual patient by combining a suitably sized pair of endplates with support columns having appropriate lengths to provide proper separation or "distraction" of the vertebrae located subjacent and suprajacent to the vertebral body defect upon fixation of the device. The support columns may be attached to the endplates by any means which provides a secure connection (e.g., by screws or with a bonding agent).

The device of the present invention may be easily installed and fixed in place according to the following method: A designated vertebral body in the thoracolumbar region of the spine and its associated disks are surgically removed and a central strut is placed between the subjacent and suprajacent vertebral bodies to maintain their correct anatomical distance. This strut may be autogenous or allograft bone or may be a removable mechanical instrument. The inventive device may then be assembled to the correct dimensions using selected support columns and endplates. The assembled device is installed by placing it into the spinal column so as to place the deep notch of the lower and upper endplates around the central strut. The device is situated within the spinal column sufficiently to completely embrace the strut. If a mechanical instrument serves as a strut, it may then be removed. However, if the strut is constructed of bone, it need not be removed but can remain and serve as bridging bone. After the device has been properly positioned, the fixation and anti-rotation screws are inserted into the threaded holes of the endplates and screwed into the neighboring vertebral bodies. Next, the small set screws are inserted into the laterally-oriented holes and tightened to further secure the axially-oriented fixation and anti-rotation screws.

After the device has been fixed into position, bone may be segmentally grafted across the notched areas of the device. Following a period of healing, the device will become completely encased within the patient's spinal column, offering secure, permanent support.

BRIEF DESCRIPTION OF THE DRAWINGS

FIG. 1 is a cross-sectional side view of a vertebral body prosthetic device according to the present invention, fixed in the spinal column of a patient.

FIG. 3 is a perspective view of another embodiment of the inventive device as assembled.

Like reference characters in the various drawings refer to like elements.

DETAILED DESCRIPTION OF THE INVENTION

Figure 2:
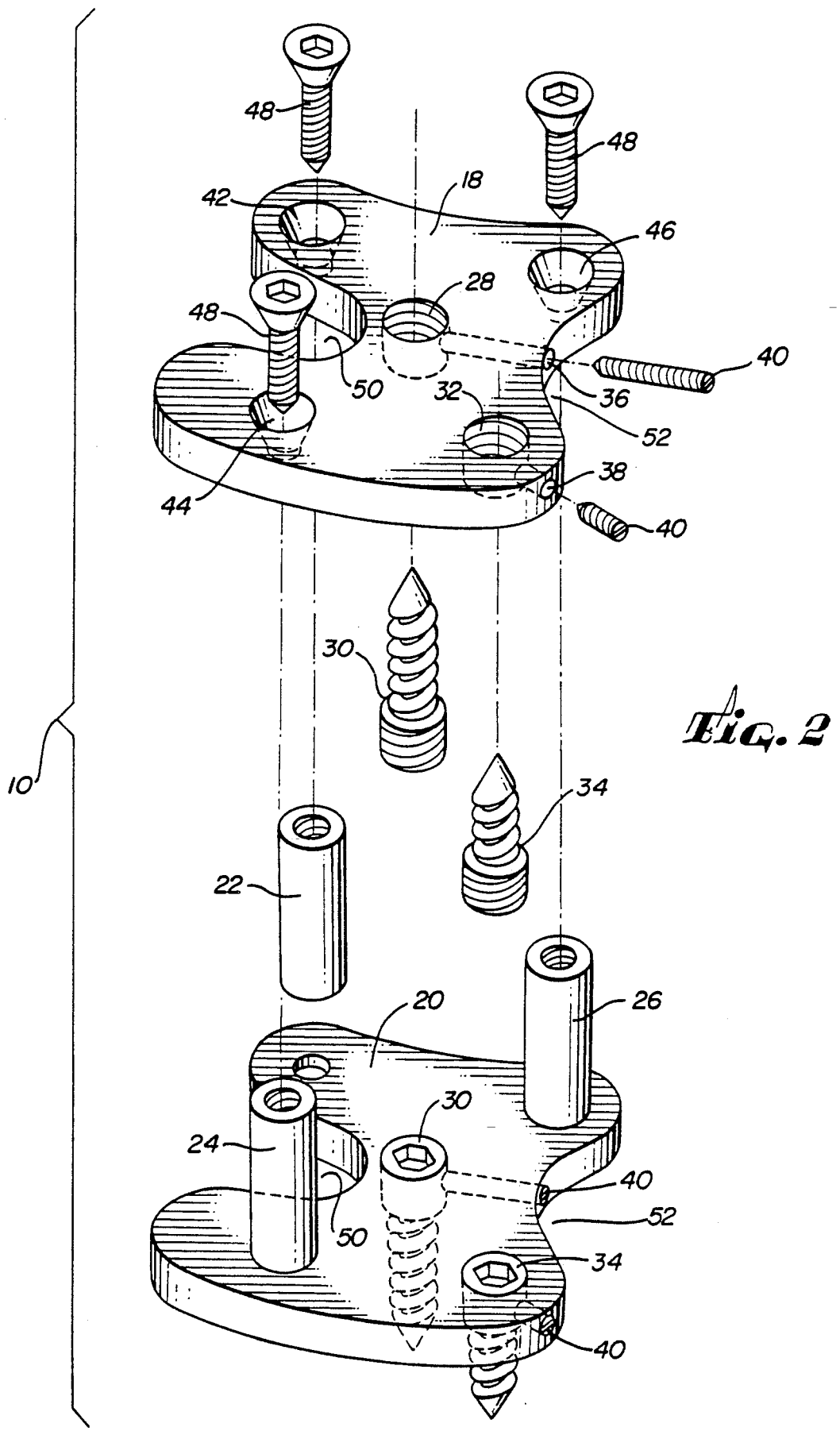
FIG. 2 is a partially exploded perspective view of the inventive device showing its components.

The following description is of the best presently contemplated mode of carrying out the invention. This description is made for the purpose of illustrating the general principles of the invention and should not be taken in a limiting sense. The scope of the invention is best determined by reference to the appended claims.

FIG. 1 shows a vertebral body prosthesis 10 according to the present invention properly positioned and fixed in the dorsi-lumbar region of a patient's spine 12. As shown, the prosthesis replaces a vertebral body and its associated subjacent and suprajacent discs and is fixed to the subjacent and suprajacent vertebral bodies 14 and 16, respectively.

The components of the inventive prosthesis can be more clearly seen in FIG. 2. In the illustrated embodiment, the device 10 comprises an upper endplate 18 and a lower endplate 20 separated by three support columns 22, 24, and 26. While the preferred embodiment utilizes three cylindrical support columns, more or fewer support columns having cylindrical or other shapes could be provided.

The upper and lower endplates 18 and 20 are identical in the illustrated embodiment. Each is provided with an upper and a lower surface and each is dimensioned to fit completely within the vertebral column of the dorsi-lumbar region of a patient's spine, i.e., the length and width of each endplate is such that when the device is inserted into a patient's spinal column in the dorsi-lumbar region, the endplates do not protrude beyond the edges of the subjacent and suprajacent vertebral bodies. While the upper and lower endplates of the illustrated embodiment are identical, endplates having different dimensions could be used to provide the desired fit.

It is desirable for the endplates to be as thin as possible yet provide adequate strength. The amount of open space between the endplates 18 and 20 may thus be maximized. It has been determined that endplates constructed of titanium having a thickness (height) of approximately 4 mm are sufficiently strong to withstand the mechanical forces to which the device is exposed when fixed within the spinal column. Furthermore, a height of approximately 4 mm allows threaded holes to be bored into the endplates for eventual screw placement.

Each endplate 18, 20 is provided with at least a first threaded hole 28 for receiving an axially-oriented fixation screw 30. The first threaded hole 28 is preferably located on the longitudinal axis of the endplate, slightly anteriorly of its lateral axis (i.e., approximately 3-4 mm offset from the lateral axis). Additionally, each endplate 18, 20 is provided with at least a second threaded hole 32 for receiving an axially-oriented anti-rotation screw 34. The second threaded hole 32 is preferably located anteriorly of the longitudinal axis of the endplate and off-set posteriorly from its lateral axis. The placement of the first and second threaded holes 28 and 32, respectively, in these approximate locations increases the stability of the device following fixation. However, the location of the threaded holes 28 and 32 may be varied as desired or required.

Fixation screw 30 and anti-rotation screw 34 are preferably shafted having a threaded tip. The heads of the screws 30 and 34 may be threaded as well to engage the threads of the holes 28 and 32, respectively. Fixation screw 30 is preferably of a length equal to or slightly exceeding the height of the subjacent and suprajacent vertebral bodies 14, 16. Anti-rotation screw 34, on the other hand, may be shorter.

Each endplate is additionally provided with two lateral passages 36 and 38. Lateral passage 36 connects to threaded hole 28 and lateral passage 38 connects to threaded hole 32. Lateral passages 36, 38 are dimensioned to receive small set screws 40 which, when inserted therein, help secure the axially-oriented screws inserted into holes 28 and 32.

In the illustrated embodiments, each endplate is further provided with three holes 42, 44 and 46. Each hole 42, 44, 46 is dimensioned to receive an axially-oriented screw 48 by which the support columns 22, 24, and 26, respectively, are connected to the endplates 18 and 20. In the illustrated embodiments, the support columns 22, 24, 26 are hollow with threaded end portions and the screws 48 are of the type having a threaded shaft to engage the threads of the end portion of the support column. However, other types of screws may be used.

While the support columns may be connected to the endplates 18, 20 by other means (e.g., by bonding), it is preferable that screws be used to allow a surgeon to custom-build the prosthesis easily by matching two properly sized endplates 18, 20 with three support columns 22, 24, 26 having lengths sufficient to provide proper distraction of the subjacent and suprajacent vertebrae 14 and 16, respectively, after fixation of the device.

Two of the holes 42, 44 are positioned to place two support columns 22, 24 posteriorly of the longitudinal axes of the endplates 18, 20, on either side of their lateral axes (i.e., in the section of the device which lies closest to the spinal cord). The third hole 46 is positioned to place the third support column 26 anteriorly of the longitudinal axes of the endplates 18, 20, offset from their lateral axes and positioned contralaterally to the hole 32 for receiving the anti-rotation screw 34.

Placement of the support columns in this arrangement maximizes the support offered by the device in the center of the patient's spinal column where most of the compressive forces are experienced. Placement of the one support column 26 anteriorly of the longitudinal axis and off-set from the lateral axis of each endplate 18, 20 permits full instrument access to the interior of the device to facilitate the placement and fixation of the axially-oriented screws 30, 34.

In two preferred embodiments of the invention (shown in FIGS. 2 and 3), each endplate 18, 20 is provided with bilateral cut-out areas. A first cut-out area forms a deep notch 50 between the holes 42 and 44 (i.e., posteriorly of the longitudinal axis, on the lateral axis of each endplate). This deep notch 50 is designed to embrace a temporary or permanent strut or instrument implanted into the spinal column to maintain the correct anatomical distance between vertebrae located subjacent and suprajacent to the vertebral defect created after a vertebral body has been removed. Notch 50 may also serve as a site for grafting bone across that side of the vertebral defect, as explained in more detail below.

A second cut-out area forms a more shallow notch 52 anteriorly of the longitudinal axis, on the lateral axis of each endplate. Notch 52 serves as a site for grafting bone on the contralateral side of the vertebral defect.

FIG. 3 illustrates another preferred embodiment of the invention wherein endplates 18 and 20 are each provided with a small ridge or fin 54 extending along their lateral axes between notches 50 and 52. Specifically, the fin 54 of the upper endplate 18 is positioned on its upper surface and the fin 54 of the lower endplate 20 is positioned on its lower surface. The small fins 54 help the device 10 resist rotation after it has been fixed into place. While the fins 54 need not be placed exactly on the lateral axis of each endplate, they should be placed in a lateral orientation so as not to impede installation of the device 10. If desired, additional fins could be provided. Alternatively, several ridge or fin pieces could be provided.

The components of the inventive device 10 may be made from a variety of materials including metal (e.g., stainless steel or titanium), high density plastics, and ceramics. Metals are the preferred materials since they may be visualized after implantation using X-ray technology. Furthermore, metals which are compatible with magnetic resonance imaging are especially preferred, e.g., titanium.

Alternatively, the components of the inventive device 10 may be made of biodegradable materials (e.g., polyglycolic acid) which are slowly degraded by the body's enzymes. Biodegradable materials, however, must remain present in stable form sufficiently long to allow bone grafts to consolidate. To promote bone growth, the materials from which the components are fabricated may be impregnated with bone growth stimulating substances (e.g., osteoblast-stimulating factor).

The device 10 of the present invention is installed and fixed as follows:

1. A designated vertebral body and its associated disks are surgically removed from the anterior approach. A standardly available vertebral body distractor is used to restore the normal distance between the vertebral bodies 14, 16 located subjacent and suprajacent to the vertebral body defect created by removal of the vertebral body. A temporary or permanent central strut is then inserted between the vertebrae 14, 16 to maintain this distance. The central strut is preferably fabricated from structural bone, e.g., autogenous or allograft bone which remains in place after fixation of the device 10 to serve as a bone graft. Alternatively, a removable mechanical instrument may serve as the central strut.

2. Next, the inventive device may be assembled from two suitably sized endplates 18, 20 and three support columns 22, 24, 26, or an appropriately-sized preassembled device 10 may be selected. The assembled device 10 is installed by placing the deep notch 50 of each endplate 18, 20 around the central strut and then placing the device into the spinal column until the strut rests snugly within the deep notches 50.

3. Since the device 10 is inserted from a lateral aspect, the small fins 54 of the embodiment illustrated in FIG. 3 are not an impediment to the installation. Instead, the fins 54 cut a small groove into the subjacent and suprajacent vertebral bodies 14, 16 as the device 10 is tapped into place. Once the device 10 has been properly installed, the fins 54 rest in their grooves providing additional rotational control for the device.

4. After the device has been properly installed, the central strut may be removed if a temporary strut was used. Then, the axially-oriented fixation screw 30 and the axially-oriented anti-rotation screw 34 are inserted into the threaded holes 28 and 32, respectively. The device 10 may then be fixed by tightening the screws 30, 34. The screws 30, 34 may be tightened using any suitable instrument such as, for example, a right angle wrench. The action of advancing the screws 30, 34 into the subjacent and suprajacent vertebral bodies effects a compressive force of the vertebrae against the respective endplates 18, 20 of the device 10.

5. Next, the small set screws 40 are inserted into the lateral passages 36 and 38 and are tightened to further fix the axially-oriented screws 30, 34.

6. After the device has been properly fixed into position, bone may be segmentally grafted across the sides of the device. Specifically, structural bone grafts may be placed in the notches 50, 52. Additionally, morselized "onlay" bone may be inserted into the open area of the device 10. Following a period of healing, the device 10 will become completely encased within the patient's spinal column, offering secure, permanent support.

The design of the inventive device provides several significant advantages over previously available devices. First, suitably-sized prosthetic devices of the present invention may be easily constructed to match the anatomic variability of vertebral bodies of substantially all patients by combining appropriately dimensioned endplates with support columns having appropriate lengths. Second, since the assembled device of the present invention is a single unit, i.e., does not include articulating components, the potential for fatigue and wear-related instability is substantially eliminated.

The open design of the inventive device provides further significant advantages over the prior art devices. First, the open design eliminates the need to include complicated drive mechanisms to drive the axially-oriented screws into the neighboring vertebrae. Instead, a surgeon installing the device may directly access the interior of the device to apply the fixation and anti-rotation screws. Second, the open design of the device permits inspection and manipulation of the spinal cord after the device has been fixed in place. Since the spinal cord can be viewed directly, the surgeon may, for example, confirm that no residual pressure is left on the spinal cord. Also, additional surgical work may be performed on the spinal cord after the device is in place since instruments may reach the spinal cord through the open area between the endplates of the device.

Moreover, the inventive device offers superior stability over prior art devices by the combination of axially-oriented fixation screws, axially-oriented anti-rotation screws and threaded holes for receiving the screws. During fixation, the action of the threads of the screws compress the subjacent and suprajacent vertebral bodies against the endplates. Thus, the subjacent and suprajacent vertebral bodies are prevented from pulling away from the endplates. The fixation and anti-rotation screws are held tightly in place by the threads of the holes of the endplates and the adjacent vertebral bodies are thus anchored to the endplates. The anti-rotation screws furthermore prevent the adjacent vertebral bodies from rotating on the endplates. Additionally, the set screws function to secure the screws to the endplates to prevent any dislodgement of the screws. The adjacent vertebral bodies are thereby prevented from angling and slipping off the endplates.

It has been determined that when the device of the present invention is properly fixed into place, it provides resistance to axial compression and flexion superior to that of an intact spine. Additionally, spines provided with the inventive device were able to resist rotation equivalent to the intact spine. In the three major planes of mobility, spines containing the inventive device either exceeded or equaled the strength of the intact spine.

Two preferred embodiments of the present invention have been illustrated and described. Nevertheless, it will be understood that various modifications may be made without departing from the spirit and scope of the invention. Accordingly, it is to be understood that the invention is not to be limited by the specific illustrated embodiment, but only by the scope of the appended claims.

We claim:

1. A vertebral body prosthetic device for replacing a surgically removed natural vertebral body, comprising:
   a. an upper endplate and a lower endplate, each endplate having a height, length and width to completely fit within a spinal column defect created when a vertebral body is surgically removed, and each endplate being provided with at least a first and a second hole extending through the height of the endplate;
   b. a plurality of support columns separating the endplates, each support column connecting to the lower surface of the upper endplate and the upper surface of the lower endplate;
   c. at least two fixation screws, one fixation screw being insertable into the first hole in the upper endplate and the other fixation screw being insertable into the first hole of the lower endplate, whereby when the device is inserted into a spinal column and the fixation screws are inserted into the first holes, the fixation screws are positioned approximately parallel to the axis of the spinal column; and
   d. at least two anti-rotation screws, one anti-rotation screw being insertable into the second hole in the upper endplate and the other anti-rotation screw being insertable into the second hole of the lower endplate, whereby when the device is inserted into a spinal column and the anti-rotation screws are inserted into the second holes, the anti-rotation screws are positioned approximately parallel to the axis of the spinal column.

2. A device according to claim 1, wherein each endplate is further provided with a plurality of lateral passages, each hole extending through the height of the endplate being connected to a respective lateral passage; and wherein the device further comprises a plurality of set screws, each insertable into one of the lateral passages, whereby when the set screws are inserted into the lateral passages, the set screws contact the screws inserted into the holes.

3. A device according to claim 1, wherein the holes in the endplates are threaded, whereby the fixation and anti-rotation screws are secured to the endplates upon insertion, and wherein the height of the endplates is sufficient only to accommodate the threads.

4. A device according to claim 1, wherein the support columns have a height to provide proper distraction of vertebrae located subjacent and suprajacent to the device when the device is inserted into the spinal column.

5. A device according to claim 4, wherein the device comprises three support columns, one support column being located anteriorly and two support columns being located posteriorly of the longitudinal axis of each endplate.

6. A device according to claim 5, wherein the posterior support columns are located on opposite sides of the lateral axis of each endplate, and wherein the anterior support column is located off-set from the lateral axis of each endplate, contralaterally of the posterior support columns.

7. A device according to claim 1, wherein each endplate includes cut-out areas.

8. A device according to claim 7, wherein each endplate includes first and second cut-out areas located contralaterally, the first cut-out area having a depth sufficient to embrace a strut used to provide proper distraction of vertebrae located subjacent and suprajacent of a vertebral defect of the spinal column into which the device is to be inserted, the second cut-out area having a more shallow depth, the first and second cut-out areas serving as sites for bilateral grafting of bone across the vertebral defect after the device is fixed in the spinal column.

9. A device according to claim 1, wherein the first hole of each endplate is located above the lateral axis of the device, on its longitudinal axis, and the second hole is located below the lateral axis of the device, off-set from its longitudinal axis.

10. A device according to claim 9, wherein the upper and lower endplates further include anti-rotation fins positioned on their upper and lower surfaces, respectively.

11. A device according to claim 10, wherein the fins are positioned along the lateral axis of each of the upper and lower endplates.

12. A device according to claim 1, wherein the endplates, the support columns, and the bone screws are made of titanium, and wherein the height of each of the upper and lower endplates is approximately 4 mm.

13. A device according to claim 1, wherein the endplates, the support columns, and the bone screws are made of high-density plastic.

14. A device according to claim 1, wherein the endplates, the support columns, and the bone screws are made of biodegradable material.

15. A device according to claim 1, wherein the fixation screws have a length approximately equal to the height of vertebral bodies located subjacent and suprajacent to the removed vertebral body.

* * * * *